(12) United States Patent
Garnier et al.

(10) Patent No.: US 6,511,669 B1
(45) Date of Patent: Jan. 28, 2003

(54) COSMETIC COMPOSITIONS CONTAINING AN ANIONIC HYDROXYALKYL ETHER SURFACTANT AND A CATIONIC POLYMER, AND USES THEREOF

(75) Inventors: Nathalie Garnier, Springfield, NJ (US); Danièle Cauwet-Martin, Paris (FR); Serge Restle, Saint-Prix (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/504,606

(22) Filed: Feb. 15, 2000

(51) Int. Cl.$^7$ ............... A61K 6/00; A61K 7/42; A61K 7/075; A01N 43/00
(52) U.S. Cl. ............ 424/401; 424/59; 510/122; 510/125; 514/183
(58) Field of Search ............... 510/122, 125; 514/183; 424/59, 401

(56) References Cited

U.S. PATENT DOCUMENTS

| | | | | |
|---|---|---|---|---|
| 4,871,536 A | * | 10/1989 | Arraudeau | 424/59 |
| 5,037,818 A | * | 8/1991 | Sime | 514/183 |
| 5,580,494 A | * | 12/1996 | Sandhu et al. | 510/125 |
| 6,022,836 A | * | 2/2000 | Dubief et al. | 510/122 |

FOREIGN PATENT DOCUMENTS

| | | |
|---|---|---|
| JP | 57-162797 | 10/1982 |
| JP | 62-149797 | 7/1987 |
| JP | 63-28008 | 11/1988 |
| JP | 63-280798 | * 11/1988 |
| JP | 4-122797 | 4/1992 |
| JP | 4-122799 | 4/1992 |
| JP | 5-92914 | 4/1993 |
| JP | 6-316546 | 11/1994 |
| JP | 7-304652 | 11/1995 |
| JP | 7-304653 | 11/1995 |
| JP | 8-3101 | 1/1996 |
| JP | 8-269487 | 10/1996 |
| JP | 8-269489 | 10/1996 |
| WO | WO-97/23193 | * 7/1997 |

OTHER PUBLICATIONS

English language Derwent Abstract of JP 57–162797. 10/82.
English language Derwent Abstract of JP 62–149797. 07/87.
English language Derwent Abstract of JP 63–28008. 11/88.
English language Derwent Abstract of JP 4–122797. 04/92.
English language Derwent Abstract of JP 4–122799. 04/92.
English language Derwent Abstract of JP 5–92914. 04/93.
English language Derwent Abstract of JP 6–316546. 11/94.
English language Derwent Abstract of JP 7–304653. 11/95.
English language Derwent Abstract of JP 7–304652. 11/95.
English language Derwent Abstract of JP 8–3101. 01/96.
English language Derwent Abstract of JP 8–269487. 10/96.
English language Derwent Abstract of JP 8–269489. 10/96.

* cited by examiner

Primary Examiner—Michael G. Hartley
Assistant Examiner—Michael A. Willis
(74) Attorney, Agent, or Firm—Finnegan, Henderson, Farabow, Garrett & Dunner, L.L.P.

(57) ABSTRACT

The invention relates to novel detergent cosmetic compositions comprising, in a cosmetically acceptable medium, at least one anionic surfactant chosen from 2-hydroxyalkyl ether carboxylic acid and salts thereof and at least one non-cellulosic cationic polymer the cationic charge density of which is greater than or equal to 2 meq/g. The invention also relates to processes for washing and/or treating keratin substances with the novel detergent cosmetic compositions.

52 Claims, No Drawings

COSMETIC COMPOSITIONS CONTAINING AN ANIONIC HYDROXYALKYL ETHER SURFACTANT AND A CATIONIC POLYMER, AND USES THEREOF

The present invention relates to novel cosmetic compositions comprising, in a cosmetically acceptable medium, at least one anionic surfactant chosen from hydroxyalkyl ether carboxylic acid and salts thereof, and at least one cationic polymer with a cationic charge density of greater than or equal to 2 meq/g.

It is common practice to use detergent compositions (shampoos or shower gels) based essentially on standard surfactants, in particular of anionic, nonionic and/or amphoteric type, but more particularly of anionic type, to clean and/or wash the hair and/or the skin. These compositions are applied to wet hair or skin, and the lather generated by massaging or rubbing with the hands removes, after rinsing with water, the various types of soiling initially present on the hair or skin.

Admittedly, these base compositions have good washing power, but the intrinsic cosmetic properties associated with them remain fairly low, in particular on account of the fact that the relatively aggressive nature of such a cleaning treatment can lead, in the long run, to more or less pronounced damage to the keratin fibers. This damage can be associated in particular with the gradual removal of the lipids or proteins contained in or at the surface of these substances.

Thus, in order to improve the cosmetic properties of the above detergent compositions, and more particularly of those which are intended to be applied to sensitized hair (i.e. hair which has been damaged or made brittle, in particular under the chemical action of atmospheric agents and/or hair treatments such as permanent-3waving, dyeing or bleaching operations), it is now common practice to introduce into these compositions additional cosmetic agents known as conditioners, which are mainly intended to repair or limit the harmful or undesirable effects induced by various treatments or attacking factors to which hair fibers may be subjected more or less repeatedly. These conditioners can also improve the cosmetic behavior of natural hair.

The conditioners most commonly used to date in shampoos are cationic polymers, silicones and/or silicone derivatives, which give washed, dry or wet hair enhanced ease of disentangling, softness and smoothness compared with that which can be obtained with the corresponding cleaning compositions from which they are absent.

However, despite the progress recently made in the field of shampoos based on cationic and/or silicone polymers, these shampoos are not really entirely satisfactory, such that there is still currently a great need to have available novel products which have better performance qualities as regards one or more of the cosmetic properties mentioned above.

Anionic surfactants of hydroxyalkyl ether carboxylic type have already been recommended in detergent cosmetic compositions. They have been described, for example, in patent applications J63280798, J08268487 and J08269482, all of which are incorporated herein by reference.

Compositions for washing the hair using these surfactants alone do not give satisfactory cosmetic properties. One object of the invention is thus to propose detergent cosmetic compositions which have improved cosmetic properties, in particular in terms of disentangling, smoothness and softness of the hair. It has been discovered that these aims can be achieved with a combination of specific cationic polymers and an anionic surfactant of hydroxyalkyl ether carboxylic type.

These novel compositions allow better application of these cationic polymers onto keratin substances (in particular the hair) than does a composition containing standard anionic surfactants such as alkyl ether carboxylate salts, without having a greasy look or feel. The compositions in accordance with the invention give keratin substances, in particular the hair, a noteworthy treating effect which is manifested in particular by ease of disentangling, as well as by the provision of volume, lightness, smoothness, softness, suppleness and hold without any lank sensation.

One subject of the invention is thus a detergent cosmetic composition, characterized in that it comprises, in a cosmetically acceptable medium, at least one non-cellulosic cationic polymer whose cationic charge density is greater than or equal to 2 meq/g, and at least one anionic surfactant chosen from 2-hydroxyalkyl ether carboxylic acid and or salts thereof.

Another subject of the invention relates to a process for treating keratin substances, such as the hair, characterized in that it consists in applying cosmetic compositions according to the invention to the said substances.

Another subject of the invention is the use of surfactants chosen from 2-hydroxyalkyl ether carboxylic acid and salts thereof in or for the manufacture of detergent cosmetic compositions comprising at least one non-cellulosic cationic polymer and whose cationic charge density is greater than or equal to 2 meq/g.

According to the present invention, the expression "keratin substances" generally refers to the hair, the eyelashes, the eyebrows, the skin, the nails, mucous membranes or the scalp, and more particularly the hair.

Various subjects of the invention will now be described in detail. All of the meanings and definitions of the compounds used in the present invention given below are valid for all the subjects of the invention.

The anionic surfactants chosen from 2-hydroxyalkyl ether carboxylic acid and salts thereof can have the following structure:

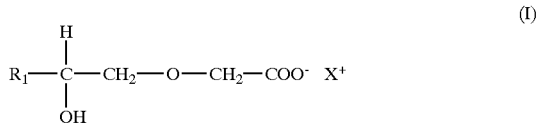

(I)

in which:

$R_1$ denotes a saturated or unsaturated, linear or branched alkyl radical comprising from 8 to 30 carbon atoms, and X denotes hydrogen or an inorganic or organic cation, such as, for example, those obtained from an alkali metal (for example $Na^+$ or $K^+$), $NH_4^+$, ammoniums obtained from basic amino acids such as lysine, arginine, sarcosine, ornithine or citrulline, or alternatively from amino alcohols such as monoethanolamine, diethanolamine, triethanolamine, glucamine, N-methylglucamine or 3-amino-1,2-propanediol.

2-Hydroxyalkyl ether carboxylic acid and salts thereof in one embodiment of the invention are compounds of formula (I) in which $R_1$ more particularly denotes a saturated or unsaturated, linear or branched alkyl radical comprising from 8 to 18 carbon atoms. Even more particularly, $R_1$ denotes a $C_8$–$C_{18}$ radical or a mixture of $C_8$–$C_{18}$ radicals derived from coconut oil.

Among the surfactants of formula (I), mention may be made of the product sold under the name Beaulight Shaa by the company Sanyo.

According to the invention, the anionic surfactant chosen from 2-hydroxyalkyl ether carboxylic acid and salts thereof can represent from 1% to 30% by weight, preferably from 3% to 15% by weight, relative to the total weight of the final composition.

The cationic polymers that can be used according to the invention have a cationic charge density of greater than or equal to 2 meq/g, preferably between 2 and 8.5 meq/g.

The cationic polymers with a cationic charge density of greater than or equal to 2 meq/g which can be used in accordance with the present invention can be chosen from any of those already known per se, i.e. in particular from those described in patent application EP-A-0 337 354 and in French patent applications FR-A-2 270 846, 2 383 660, 2 598 611, 2 470 596 and 2 519 863, all or which are incorporated herein by reference.

Even more generally, for the purposes of the present invention, the expression "cationic polymer" denotes any polymer containing cationic groups and/or groups that can be ionized into cationic groups.

The preferred cationic polymers are chosen from those that contain units comprising primary, secondary, tertiary and/or quaternary amine groups that can either form part of the main polymer chain or can be borne by a side substituent directly connected thereto.

The cationic polymers used generally have a number-average molecular mass of between approximately 500 and approximately $5\times10^6$, and preferably between approximately $10^3$ and approximately $3\times10^6$.

Among the cationic polymers, mention may be made more particularly of polymers of the polyamine, polyamino amide and polyquaternary ammonium type. These are known products.

The polymers of polyamine, polyamino amide and polyquaternary ammonium type which can be used in accordance with the present invention and which can be mentioned in particular are those described in French patent No. 2 505 348 or 2 542 997, all of which are incorporated herein by reference. Examples of such polymers are set forth below.

(1) Quaternized or non-quaternized vinylpyrrolidone/dialkylaminoalkyl acrylate or methacrylate copolymers.

(2) Polymers consisting of piperazinyl units and of divalent alkylene or hydroxyalkylene radicals containing straight or branched chains, optionally interrupted by oxygen, sulphur or nitrogen atoms or by aromatic or heterocyclic rings, as well as the oxidation and/or quatemization products of these polymers. Such polymers are described, in particular, in French patents 2,162,025 and 2,280,361, both of which are incorporated herein by reference.

(3) Water-soluble polyamino amides prepared in particular by polycondensation of an acidic compound with a polyamine; these polyamino amides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; the crosslinking agent is used in proportions ranging from 0.025 to 0.35 mol per amine group of the polyamino amide; these polyamino amides can be alkylated or, if they contain one or more tertiary amine functions, they can be quaternized. Such polymers are described, in particular, in French patents 2,252,840 and 2,368,508, all of which are incorporated herein by reference.

(4) The polyamino amide derivatives resulting from the condensation of polyalkylene polyamines with polycarboxylic acids followed by alkylation with difunctional agents. Mention may be made, for example, of adipic acid/dialkylaminohydroxyalkyldialkylenetriamine polymers in which the alkyl radical contains from 1 to 4 carbon atoms and preferably denotes methyl, ethyl or propyl. Such polymers are described in particular in French patent 1,583,363. Among these derivatives, mention may be made more particularly of the adipic acid/dimethylamino-hydroxypropyl/diethylenetriamine polymers sold under the name "Cartaretine F, F4 or F8" by the company Sandoz.

(5) The polymers obtained by reaction of a polyalkylene polyamine containing two primary amine groups and at least one secondary amine group with a dicarboxylic acid chosen from diglycolic acid and saturated aliphatic dicarboxylic acids having from 3 to 8 carbon atoms. The molar ratio between the polyalkylene polyamine and the dicarboxylic acid is between 0.8:1 and 1.4:1; the polyamino amide resulting therefrom is reacted with epichlorohydrin in a molar ratio of epichlorohydrin relative to the secondary amine group of the polyamino amide of between 0.5:1 and 1.8:1. Such polymers are described in particular in U.S. Pat. Nos. 3,227,615 and 2,961,347. Polymers of this type are sold in particular under the name "Hercosett 57" by the company Hercules Inc. or alternatively under the name "PD 170" or "Delsette 101" by the company Hercules in the case of the adipic acid/epoxypropyl/diethylenetriamine copolymer.

(6) Cyclopolymers of alkyldiallylamine or of dialkyldiallylammonium, such as the homopolymers or copolymers containing, as main constituent of the chain, units corresponding to formula (II) or (III):

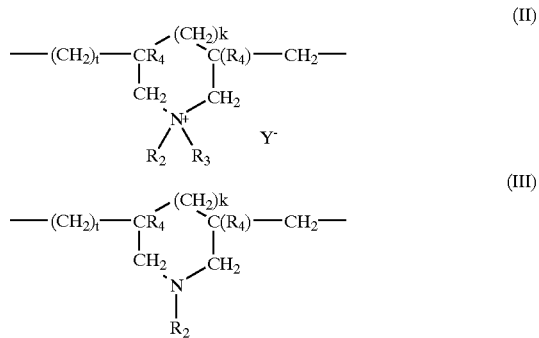

in which k and t are equal to 0 or 1, the sum k+t being equal to 1; $R_4$ denotes a hydrogen atom or a methyl radical; $R_2$ and $R_3$, which may be identical or different, denote an alkyl group having from 1 to 22 carbon atoms, a hydroxyalkyl group in which the alkyl group preferably has 1 to 5 carbon atoms, or a lower ($C_1$–$C_4$) amidoalkyl group, or $R_2$ and $R_3$ can denote, together with the nitrogen atom to which they are attached, heterocyclic groups such as piperidyl or morpholinyl; $Y^-$ is an anion such as bromide, chloride, acetate, borate, citrate, tartrate, bisulphate, bisulphite, sulphate or phosphate. These polymers are described in particular in French patent 2,080,759 and in its Certificate of Addition 2,190,406, both of which are incorporated herein by reference.

$R_2$ and $R_3$, which may be identical or different, preferably denote an alkyl group containing from 1 to 4 carbon atoms.

Among the polymers defined above, mention may be made more particularly of the dimethyldiallylammonium chloride homopolymer sold under the name "Merquat 100" by the company Calgon (and its homologues of low weight-average molecular masses) and the copolymers of diallyldimethylammonium chloride and of acrylamide sold under the name "Merquat 550" by the company Calgon.

(7) The quaternary diammonium polymer containing repeating units corresponding to formula (IV):

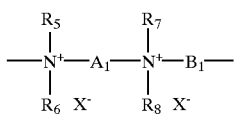

in which:
- $R_5$, $R_6$, $R_7$ and $R_8$, which may be identical or different, represent aliphatic, alicyclic or arylaliphatic radicals containing from 1 to 20 carbon atoms or lower hydroxyalkylaliphatic radicals, or alternatively $R_5$, $R_6$, $R_7$ and $R_8$, together or separately, constitute, with the nitrogen atoms to which they are attached, heterocycles optionally containing a second heteroatom other than nitrogen, or alternatively $R_5$, $R_6$, $R_7$ and $R_8$ represent a linear or branched $C_1$–$C_6$ alkyl radical substituted with a nitrile, ester, acyl or amide group or a group —CO—O—$R_9$—D or —CO—NH—$R_9$—D where $R_9$ is an alkylene and D is a quaternary ammonium group;
- $A_1$ and $B_1$ represent polymethylene groups containing from 2 to 20 carbon atoms which may be linear or branched, saturated or unsaturated, and which may contain, linked to or intercalated in the main chain, one or more aromatic rings or one or more oxygen or sulphur atoms or sulphoxide, sulphone, disulphide, amino, alkylamino, hydroxyl, quaternary ammonium, ureido, amide or ester groups, and
- $X^-$ denotes an anion derived from an inorganic or organic acid;
- $A_1$, $R_5$ and $R_7$ can form, with the two nitrogen atoms to which they are attached, a piperazine ring; in addition, if $A_1$ denotes a linear or branched, saturated or unsaturated alkylene or hydroxyalkylene radical, $B_1$ can also denote a group $$(CH_2)_n\text{—CO—D—OC—}(CH_2)_n\text{—}$$

in which D is chosen from:
a) a glycol residue of formula: —O—Z—O—, where Z denotes a linear or branched hydrocarbon radical or a group corresponding to one of the following formulae:

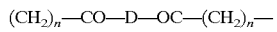

—[CH$_2$—CH(CH$_3$)—O]$_y$—CH$_2$—CH(CH$_3$)— where x and y denote an integer from 1 to 4, representing a defined and unique degree of polymerization or any number from 1 to 4 representing an average degree of polymerization;
b) a bis-secondary diamine residue such as a piperazine derivative;
c) a bis-primary diamine residue of formula: —NH—Y—NH—, where Y denotes a linear or branched hydrocarbon radical, or alternatively the divalent radical —CH$_2$—CH$_2$—S—S—CH$_2$—CH$_2$—; and
d) a ureylene group of formula: —NH—CO—NH—.

Preferably, $X^-$ is an anion such as chloride or bromide.

These polymers generally have a number-average molecular mass of between 1000 and 100,000. Polymers of this type are described in particular in French patents 2,320,330, 2,270,846, 2,316,271, 2,336,434 and 2,413,907 and U.S. Pat. Nos. 2,273,780, 2,375,853, 2,388,614, 2,454, 547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020, all or which are incorporated herein by reference.

The polymers that can be used more particularly are those consisting of repeating units corresponding to the formula (V):

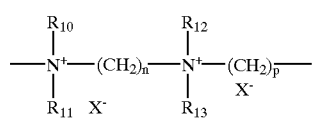

in which $R_{10}$, $R_{11}$, $R_{12}$ and $R_{13}$, which may be identical or different, denote an alkyl or hydroxyalkyl radical containing from 1 to 4 carbon atoms approximately, n and p are integers ranging from 2 to 20 approximately and $X^-$ is an anion derived from an inorganic or organic acid.

In one embodiment of formula (V), $R_{10}$, $R_{11}$, $R_{12}$ and $R_{13}$ represent a methyl radical and n=3, p=6 and X=Cl, known as hexadimethrine chloride according to the INCI (CTFA) name.

(8) Quaternary polyammonium polymers consisting of units of formula (VI):

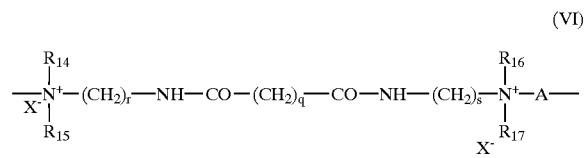

in which:

$R_{14}$, $R_{15}$, $R_{16}$ and $R_{17}$, which may be identical or different, represent a hydrogen atom or a methyl, ethyl, propyl, β-hydroxyethyl, β-hydroxypropyl or —CH$_2$CH$_2$(OCH$_2$CH$_2$)$_p$OH radical, p is equal to 0 or to an integer between 1 and 6, with the proviso that $R_{14}$, $R_{15}$, $R_{16}$ and $R_{17}$ do not simultaneously represent a hydrogen atom, r and s, which may be identical or different, are integers between 1 and 6, q is equal to 0 or to an integer between 1 and 34, $X^-$ denotes an anion such as a halide, and A denotes a radical derived from a dihalide or preferably represents —CH$_2$—CH$_2$—O—CH$_2$—CH$_2$—.

Such compounds are described in particular in patent application EP-A-122,324, incorporated herein by reference. Among these products, mention may be made, for example, of "Mirapol® A 15", "Mirapol® AD1", "Mirapol® AZ1" and "Mirapol® 175" sold by the company Miranol.

(9) Homopolymers or copolymers containing at least 1 unit derived from acrylic or methacrylic acids and chosen from:

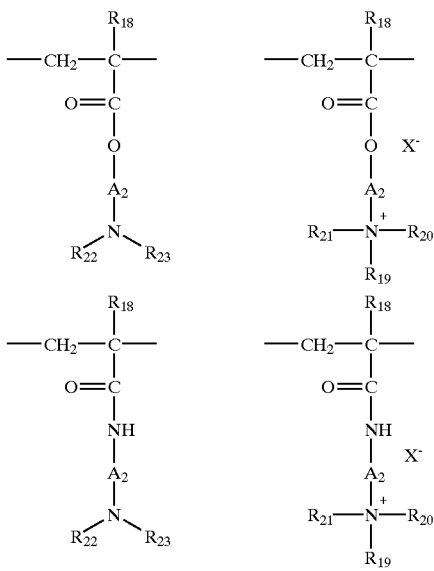

in which:
  the groups $R_{18}$, which may be identical or different, denote H or $CH_3$
  the groups $A_2$ independently denote a linear or branched alkyl group of 1 to 6 carbon atoms or a hydroxyalkyl group of 1 to 4 carbon atoms,
  the groups $R_{19}$, $R_{20}$ and R21, which may be identical or different, independently denote an alkyl group of 1 to 18 carbon atoms or a benzyl radical,
  the groups $R_{22}$ and $R_{23}$, which may be identical or different, represent a hydrogen atom or an alkyl group of 1 to 6 carbon atoms, and
  X denotes an anion, for example methosulphate or halide, such as chloride or bromide.

The comonomer(s) which can be used in the preparation of the corresponding copolymers belong to the family of acrylamides, methacrylamides, diacetone acrylamides, acrylamides and methacrylamides substituted on the nitrogen with lower alkyls, alkyl esters, acrylic or methacrylic acids, vinylpyrrolidone or vinyl esters.

(10) Quaternary polymers of vinylpyrrolidone and of vinylimidazole, such as, for example, the product sold under the name Luviquat® FC 370 by the company BASF.

(11) Crosslinked polymers of methacryloyloxy($C_1$–$C_4$) alkyltri($C_1$–$C_4$)alkylammonium salts such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound containing olefinic unsaturation, in particular methylenebisacrylamide. A crosslinked acrylamide/methacryloyloxyethyltrimethylammonium chloride copolymer (20/80 by weight) in the form of a dispersion containing 50% by weight of the said copolymer in mineral oil can be used more particularly. This dispersion is sold under the name "Salcare® SC 92" by the company Allied Colloids. A crosslinked methacryloyloxyethyltrimethylammonium chloride homopolymer containing about 50% by weight of the homopolymer in mineral oil or in a liquid ester can also be used. These dispersions are sold under the name "Salcare® SC 95" by the company Allied Colloids.

(12) Other cationic polymers that can be used in the context of the invention are polyalkyleneimines, in particular polyethyleneimines, polymers containing vinylpyridine or vinylpyridinium units, condensates of polyamines and of epichlorohydrin, quaternary polyureylenes and chitin derivatives.

Among all the cationic polymers that can be used in the context of the present invention, it is preferred to use cyclopolymers, in particular dimethyldiallylammonium chloride polymers or copolymers of dimethyidiallylammonium chloride and of acrylamide, sold under the names "Merquat 100" and "Merquat 550" by the company Calgon.

According to the invention, the cationic polymer can represent from 0.001% to 10% by weight, preferably from 0.005% to 5% by weight and even more preferably from 0.01% to 3% by weight, relative to the total weight of the final composition.

The compositions of the invention also advantageously contain at least one other surfactant, which is generally present in an amount of between 0.1% and 40% by weight approximately, preferably between 3% and 30% and even more preferably between 5% and 20%, relative to the total weight of the composition.

This surfactant can be chosen from anionic, amphoteric, nonionic and cationic surfactants, or mixtures thereof.

The additional surfactants that are suitable for carrying out the present invention are, in particular, the following:
(i) Anionic Surfactant(s):

In the context of the present invention, their nature is generally not of critical importance.

Thus, as examples of anionic surfactants which can be used, alone or as mixtures, in the context of the present invention, mention may be made in particular (non-limiting list) of salts (in particular alkaline salts, especially sodium salts, ammonium salts, amine salts, aminoalcohol salts or magnesium salts) of the following compounds: alkyl sulphates, alkyl ether sulphates, alkylamidoether sulphates, alkylarylpolyether sulphates, monoglyceride sulphates; alkyl sulphonates, alkyl phosphates, alkylamide sulphonates, alkylaryl sulphonates, α-olefin sulphonates, paraffin sulphonates; alkyl sulphosuccinates, alkyl ether sulphosuccinates, alkylamide sulphosuccinates; alkyl sulphosuccinamates; alkyl sulphoacetates; alkyl ether phosphates; acyl sarcosinates; acyl isethionates and N-acyltaurates, the alkyl or acyl radical of all of these various compounds preferably containing from 8 to 24 carbon atoms, and the aryl radical preferably denoting a phenyl or benzyl group. Among the anionic surfactants which can also be used, mention may also be made of fatty acid salts such as the salts of oleic, ricinoleic, palmitic and stearic acids, coconut oil acid or hydrogenated coconut oil acid; acyl lactylates in which the acyl radical contains 8 to 20 carbon atoms. Weakly anionic surfactants can also be used, such as alkyl-D-galactosiduronic acids and their salts, as well as polyoxyalkylenated ($C_6$–$C_{24}$) alkyl ether carboxylic acids, polyoxyalkylenated ($C_6$–$C_{24}$) alkylaryl ether carboxylic acids, polyoxyalkylenated ($C_6$–$C_{24}$) alkylamido ether carboxylic acids and their salts, in particular those containing from 2 to 50 ethylene oxide groups, and mixtures thereof.

Among the anionic surfactants, it is preferred according to the invention to use alkyl sulphate salts and alkyl ether sulphate salts and mixtures thereof.
(ii) Nonionic surfactant(s):

The nonionic surfactants are, themselves also, compounds that are well known per se (see in particular in this respect "Handbook of Surfactants" by M. R. Porter, published by Blackie & Son (Glasgow and London), 1991, pp. 116–178) and, in the context of the present invention, their nature is generally not a critical feature. Thus, they can be chosen in particular from (non-limiting list) polyethoxylated, polypropoxylated or polyglycerolated fatty acids, alkylphenols, ?-diols or alcohols having a fatty chain containing, for example, 8 to 18 carbon atoms, it being possible for the number of ethylene oxide or propylene oxide groups to range in particular from 2 to 50 and for the number of glycerol groups to range in particular from 2 to 30. Mention may also be made of copolymers of ethylene oxide and of propylene oxide, condensates of ethylene oxide and of propylene oxide with fatty alcohols; polyethoxylated fatty amides preferably having from 2 to 30 mol of ethylene oxide, polyglycerolated fatty amides containing on average 1 to 5, and in particular 1.5 to 4, glycerol groups; polyethoxylated fafty amines preferably having 2 to 30 mol of ethylene oxide; oxyethylenated fatty acid esters of sorbitan having from 2 to 30 mol of ethylene oxide; fatty acid esters of sucrose, fatty acid esters of polyethylene glycol, alkylpolyglycosides, N-alkylglucamine derivatives, amine oxides such as ($C_{10}$–$C_{14}$)alkylamine oxides or N-acylaminopropylmorpholine oxides. It will be noted that the alkylpolyglycosides constitute nonionic surfactants that are particularly suitable in the context of the present invention.

(iii) Amphoteric Surfactant(s):

The additional amphoteric surfactants, whose nature is generally not a critical feature in the context of the present invention, can be, in particular (non-limiting list), aliphatic secondary or tertiary amine derivatives in which the aliphatic radical is a linear or branched chain containing 8 to 22 carbon atoms and containing at least one water-soluble anionic group (for example carboxylate, sulphonate, sulphate, phosphate or phosphonate); mention may also be made of ($C_8$–$C_{20}$)alkylbetaines, sulphobetaines, ($C_8$–$C_{20}$) alkylamido($C_1$–$C_6$)alkylbetaines or ($C_8$–$C_{20}$)alkylamido ($C_1$–$C_6$)alkylsulphobetaines.

Among the amine derivatives, mention may be made of the products sold under the name Miranol, as described in U.S. Pat. Nos. 2,528,378 and 2,781,354 and having the structures:

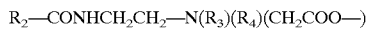

$R_2$—CONHCH$_2$CH$_2$—N($R_3$)($R_4$)(CH$_2$COO—)

in which: $R_2$ denotes an alkyl radical derived from an acid $R_2$—COOH present in hydrolysed coconut oil, for example, a saturated or unsaturated, linear or branched ($C_5$–$C_{19}$)alkyl radical, a heptyl, nonyl or undecyl radical, $R_3$ denotes a β-hydroxyethyl group and $R_4$ denotes a carboxymethyl group; and

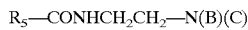

$R_5$—CONHCH$_2$CH$_2$—N(B)(C)

in which B represents —CH$_2$CH$_2$OX', C represents —(CH$_2$)$_z$—Y', with z=1 or 2, X' denotes the —CH$_2$CH$_2$—COOH group or a hydrogen atom, Y' denotes —COOH or the —CH$_2$—CHOH—SO$_3$H radical, and $R_5$ denotes an alkyl radical of a carboxylic acid present in coconut oil or in hydrolysed linseed oil, for example, a saturated or unsaturated, linear or branched ($C_5$–$C_{19}$)alkyl radical, an alkyl radical, in particular a $C_7$, $C_9$, $C_{11}$ or $C_{13}$ alkyl radical, a $C_{17}$ alkyl radical and its iso form, an unsaturated $C_{17}$ radical.

These compounds are classified in the CTFA dictionary, 5th edition, 1993, under the names disodium cocoamphodiacetate, disodium lauroamphodiacetate, disodium caprylamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid, and cocoamphodipropionic acid.

By way of example, mention may be made of the cocoamphodiacetate sold under the trade name Miranol® C2M concentrate by the company Rhodia Chimie.

Mixtures of surfactants are used in one embodiment of the compositions of the invention, in particular mixtures of anionic surfactants and mixtures of anionic surfactants and of amphoteric or nonionic surfactants.

The additional anionic surfactant used is preferably chosen from the ($C_{12}$–$C_{14}$)alkyl sulphates of sodium, of triethanolamine or of ammonium, the ($C_{12}$–$C_{14}$)alkyl ether sulphates of sodium, of triethanolamine or of ammonium oxyethylenated with 2.2 mol of ethylene oxide, sodium cocoyl isethionate and sodium ($C_{14}$–$C_{16}$)-α-olefin sulphonate, and mixtures thereof, with:

either an amphoteric surfactant such as the amine derivatives known as disodium cocoamphodipropionate or sodium cocoamphopropionate, sold in particular by the company Rhodia Chimie under the trade name "Miranol® C2M Conc." as an aqueous solution containing 38% active material, or under the name Miranol® C32;

or an amphoteric surfactant, such as alkylbetaines, in particular the cocobetaine sold under the name "Dehyton® AB 30" as an aqueous solution containing 32% AM by the company Henkel or such as ($C_8$–$C_{20}$)-alkylamido($C_1$–$C_6$)alkylbetaines, in particular Tegobetaine® F 50 sold by the company Goldschmidt.

Cationic surfactants can also be used, among which mention may be made in particular (non-limiting list) of: optionally polyoxyalkylenated primary, secondary or tertiary fafty amine salts; quaternary ammonium salts such as tetraalkylammonium, alkylamidoalkyltrialkylammonium, trialkylbenzylammonium, trialkylhydroxyalkylammonium or alkylpyridinium chlorides or bromides; imidazoline derivatives; or amine oxides of cationic nature.

The at least one anionic surfactant other than the 2-hydroxyalkyl ether carboxylic acid or salts thereof is generally present in a proportion of from 1 to 30% by weight, preferably from 3 to 15% by weight, relative to the total weight of the composition.

The at least one amphoteric or nonionic surfactant is generally present in a proportion of from 0.5 to about 15% by weight, preferably from 1 to 5% by weight, relative to the total weight of the composition.

The quantity and quality of the surfactants are those which are sufficient to give the final composition satisfactory foaming and/or detergent power.

In the composition according to the present invention, the detergent surfactants generally represent in total from 4 to 50% by weight and preferably from 6 to 35% by weight and more particularly from 8 to 25% by weight relative to the total weight of the composition.

The composition of the invention can also contain at least one additive chosen from thickeners, fragrances, nacres, preserving agents, sunscreens, anionic, nonionic or amphoteric polymers, cationic polymers with a charge density of less than 2 meq/g, proteins, protein hydrolysates, ceramides, pseudoceramides, fatty acids containing linear or branched $C_{16}$–$C_{40}$ chains, such as 18-methyleicosanoic acid, hydroxy acids, vitamins, panthenol, silicones, plant oils, mineral oils and synthetic oils, antidandruff agents and any other additive conventionally used in cosmetics which does not affect the stability and properties of the compositions according to the invention.

These additives are present in the composition according to the invention in proportions which can range from 0 to 50% by weight relative to the total weight of the composition. The precise amount of each additive is readily determined by a person skilled in the art on the basis of its nature and its function.

The cosmetically acceptable medium can consist solely of water or of a mixture of water and of a cosmetically acceptable solvent such as a $C_1$–$C_4$ lower alcohol, for instance ethanol, isopropanol, tert-butanol or n-butanol; alkylene glycols, for instance propylene glycol, and glycol ethers.

Preferably, the composition comprises from 50 to 95% by weight of water relative to the total weight of the composition.

The detergent compositions according to the invention have a final pH generally of between 3 and 10. Preferably, this pH is between 4 and 8. Adjustment of the pH to the desired value can be carried out conventionally by adding a base (organic or inorganic) to the composition, for instance aqueous ammonia or a primary, secondary or tertiary (poly)amine, for instance monoethanolamine, diethanolamine, triethanolamine, isopropanolamine or 1,3-propanediamine, or alternatively by adding an acid, preferably a carboxylic acid such as, for example, citric acid.

In addition to the combination defined above, the compositions in accordance with the invention can contain viscosity modifiers such as electrolytes or thickeners. Mention may be made in particular of sodium chloride, sodium xylenesulphonate, scleroglucans, xanthan gums, fatty acid alkanolamides, alkyl ether carboxylic acid alkanolamides optionally oxyethylenated with up to 5 mol of ethylene oxide, such as the products sold under the name "Aminol A15" by the company Chem Y, crosslinked polyacrylic acids and crosslinked acrylic acid/$C_{10}$–$C_{30}$ alkyl acrylate copolymers. These viscosity modifiers are used in the compositions according to the invention in proportions which can range up to 10% by weight relative to the total weight of the composition.

The compositions in accordance with the invention can also contain up to 5% of nacres or opacifiers that are well known in the state of the art, such as, for example, sodium or magnesium palmitate, sodium or magnesium stearate or hydroxystearate, acyl derivatives containing a fatty chain, such as ethylene glycol or polyethylene glycol monostearate or distearate, and ethers containing fatty chains such as, for example, distearyl ether or 1-(hexadecyloxy)-2-octadecanol.

The compositions according to the invention can also contain foam synergists such as $C_{10}$–$C_{18}$ 1,2-alkanediols or fatty alkanolamides derived from mono- or diethanolamine.

The compositions in accordance with the invention can be used for washing and treating keratin substances such as the hair, the skin, the eyelashes, the eyebrows, the nails, the lips or the scalp, and more particularly the hair.

In addition, the detergent compositions according to the invention are shampoos, shower gels and bubble baths.

The compositions of the invention can also be in the form of rinse-out or lave-in conditioners, permanent-waving, hair-straightening, dyeing or bleachinge compositions, or alternatively in the form of rinse-out compositions to be applied before or after dyeing, bleaching, permanent-waving or straightening the hair or between the two steps of a permanent-waving or hair-straightening operation.

The compositions of the invention can also be in the form of make-up-removing products.

The compositions according to the invention can be in the form of a gel, a milk, a cream, an emulsion, a thickened lotion or a mousse and can be used for the skin, the scalp, the nails, the eyelashes, the lips and, more particularly, the hair.

These detergent compositions are preferably foaming and the foaming power of the compositions according to the invention, characterized by a foam height, is generally greater than 75 mm, preferably greater than 100 mm, measured according to the modified Ross-Miles method (NF T 73-404/ISO696). The modifications to the method are as follows:

The measurement is carried out at a temperature of 22° C. with osmosed water. The concentration of the solution is 2 g/l. The drop height is 1 m. The amount of composition which is dropped is 200 ml. These 200 ml of composition fall into a measuring cylinder with a diameter of 50 mm and containing 50 ml of the composition to be tested. The measurement is carried out 5 minutes after stopping the flow of the composition.

Another subject of the invention is a process for treating keratin substances such as the skin or the hair, characterized in that it consists in applying a cosmetic composition as defined above to the keratin substances, optionally followed by carrying out a rinsing operation, in particular with water.

Thus, this process according to the invention allows the treatment, care, washing of or removal of make-up from the skin, the hair or any other keratin substance.

In all of the text hereinabove and hereinbelow, the percentages expressed are on a weight basis.

The invention will now be illustrated more fully with the aid of the examples which follow, which cannot be considered as limiting it to the embodiments described. In the examples, AM means active material.

EXAMPLE 1

Two shampoo compositions were prepared, one in accordance with the invention and the other (B) a comparative composition:

|  | A Invention | B Comparative |
|---|---|---|
| Akyposoft 45 NV from KAO | — | 15 gAM |
| Sodium 2-(2-hydroxylauryloxy)acetate Beaulight SHAA from Sanyo | 15 gAM | — |
| Merquat 550 from Calgon | 1 gAM | 1 gAM |
| Citric acid qs pH | 7 | 7 |
| Demineralized water qs | 100 g | 100 g | wherein Akyposoft 45 NV (KAO)is sodium lauryl ether carboxylate containing 4.5 EO, as an aqueous solution containing 22% active material;

Beaulight SHAA from Sanyo is sodium 2-(2-hydroxylauryloxy)acetate, as an aqueous solution containing 30% active material; and Merquat 550 is copolymer of diallyidimethylammonium chloride and of acrylamide, sold by Calgon (cationic charge density≅3.5 meq/g).

A shampoo wash was carried out by applying about 1 g of composition A or composition B to locks (2.5 g) of bleached hair which have been moistened beforehand. The shampoo was worked into a lather, left on the hair for 10 minutes and then rinsed out thoroughly with running water.

The disentangling of wet hair treated with these two shampoos was then compared by means of a sensory evaluation test.

The object of the test used was to classify, by jury, each series of two samples by attributing a grade of 1 to the lock which disentangles most easily and a grade of 2 to the lock which disentangles least easily. The two locks of the same series were presented simultaneously to the judge. Statistical analysis of the results was carried out with the aid of the tables by A. Kramer (Food Technology 17-(12), 124–125, 1963).

The 10 testers unanimously declared that the hair washed with composition A was significantly easier to disentangle than that treated with composition B.

EXAMPLE 2

A shampoo composition A in accordance with the invention was prepared:

|  | A Invention |
|---|---|
| Sodium lauryl ether sulphate containing 2.2 mol of EO, as an aqueous solution containing 70% active material | 4 gAM |
| Sodium 2-(2-hydroxylauryloxy)acetate Beaulight SHAA from Sanyo | 10 gAM |
| Mexomer PO from Chimex | 0.6 gAM |
| Xanthan gum | 1 g |
| Demineralized water qs | 100 g | wherein Beaulight SHAA from Sanyo is sodium 2-(2-hydroxylauryloxy) acetate, as an aqueous solution containing 30% active material; and Mexomer PO is hexadimethrine chloride as an aqueous solution containing 60% active material (cationic charge density≅7.2 meq/g).

What is claimed is:

1. A detergent cosmetic composition comprising at least one non-cellulosic cationic polymer with a cationic charge density of greater than or equal to 2 meq/g, and at least one anionic surfactant chosen from 2-hydroxyalkyl ether carboxylic acids and salts thereof.

2. A composition according to claim 1, wherein said at least one anionic surfactant has the following structure:

$$R_1-\underset{\underset{OH}{|}}{\overset{\overset{H}{|}}{C}}-CH_2-O-CH_2-COO^-\ X^+ \quad (I)$$

wherein $R_1$ denotes a saturated or unsaturated, linear or branched alkyl radical comprising from 8 to 30 carbon atoms; and X denotes hydrogen or an inorganic or organic cation.

3. A composition according to claim 2, wherein said radical $R_1$ denotes a saturated or unsaturated, linear or branched alkyl radical comprising from 8 to 18 carbon atoms.

4. A composition according to claim 2, wherein said radical $R_1$ is a radical derived from coconut oil.

5. A composition according claim 1, wherein said at least one non-cellulosic cationic polymer has a cationic charge density of between about 2 and 8.5 meq/g.

6. A composition according to claim 1, wherein said at least one non-cellulosic cationic polymer comprises quaternized or non-quaternized vinylpyrrolidone/dialkylaminoalkyl acrylate or methacrylate copolymers.

7. A composition according to claim 1, wherein said at least one non-cellulosic cationic polymer comprises piperazinyl units and divalent alkylene or hydroxyalkylene radicals containing straight or branched chains, optionally interrupted by oxygen, sulphur or nitrogen atoms or by aromatic or heterocyclic rings, and optionally the oxidation and/or quaternization products of these polymers.

8. A composition according to claim 1, wherein said at least one non-cellulosic cationic polymer comprises water-soluble polyamino amides.

9. A composition according to claim 8, wherein said water-soluble polyamino amides are prepared by polycondensation of an acidic compound with a polyamine.

10. A composition according to claim 9, wherein said water-soluble polyamino amides are crosslinked with an epihalohydrin, a diepoxide, a dianhydride, an unsaturated dianhydride, a bis-unsaturated compound, a bis-halohydrin, a bis-azetidinium, a bis-haloacyidiamine, or a bis-alkyl halide.

11. A composition according to claim 9, wherein said water-soluble polyamino amides are crosslinked with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated compound.

12. A composition according to claim 9, wherein the crosslinking agent is used in proportions ranging from 0.025 to 0.35 mol per amine group of the polyamino amide.

13. A composition according to claim 9, wherein said water-soluble polyamino amides are alkylated.

14. A composition according to claim 9, wherein said water-soluble polyamino amides contain one or more tertiary amine functions and are optionally quaternized.

15. A composition according to claim 1, wherein said at least one non-cellulosic cationic polymer comprises polyamino amide derivatives resulting from the condensation of polyalkylene polyamines with polycarboxylic acids followed by alkylation with difunctional agents.

16. A composition according to claim 1, wherein said at least one non-cellulosic cationic polymer comprises polymers obtained by reaction of a polyalkylene polyamine containing two primary amine groups and at least one secondary amine group with a dicarboxylic acid chosen from diglycolic acid and saturated aliphatic dicarboxylic acids having from 3 to 8 carbon atoms.

17. A composition according to claim 16, wherein the molar ratio between said polyalkylene polyamine and said dicarboxylic acid is between 0.8:1 and 1.4:1.

18. A composition according to claim 16, wherein the polyamino amide resulting therefrom is reacted with epichlorohydrin in a molar ratio of epichlorohydrin relative to the secondary amine group of the polyamino amide of between 0.5:1 and 1.8:1.

19. A composition according to claim 1, wherein said at least one non-cellulosic cationic polymer comprises homopolymers or copolymers of units corresponding to formula (II) or (III):

$$-(CH_2)_t-CR_4\underset{\underset{\underset{R_2}{/}\underset{R_3}{\backslash}}{CH_2\ \ \ CH_2}}{\overset{(CH_2)_k}{\diagup\diagdown}}C(R_4)-CH_2-\quad Y^- \quad (II)$$

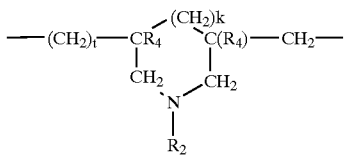

(III)

wherein:
k and t are equal to 0 or 1, the sum k+t being equal to 1;
$R_4$ denotes a hydrogen atom or a methyl radical;
$R_2$ and $R_3$, which may be identical or different, denote an alkyl group having from 1 to 22 carbon atoms, a hydroxyalkyl group in which the alkyl group has 1 to 5 carbon atoms, a lower ($C_1$-$C_4$) amidoalkyl group, or heterocyclic groups, together with the nitrogen atom to which they are attached; and
$Y^-$ denotes an anion.

20. A composition according to claim 19, wherein $R_2$ and $R_3$ denote, together with the nitrogen atom to which they are attached, the heterocyclic groups piperidyl or morpholinyl.

21. A composition according to claim 1, wherein said at least one non-cellulosic cationic polymer comprises a quaternary diammonium polymer containing repeating units corresponding to formula (IV):

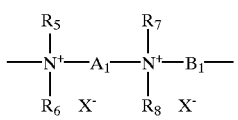

(IV)

wherein
$R_5$, $R_6$, $R_7$ and $R_8$, which may be identical or different, are chosen from aliphatic, alicyclic or arylaliphatic radicals containing from 1 to 20 carbon atoms or lower hydroxyalkylaliphatic radicals; heterocycles together with the nitrogen atoms to which they are attached which optionally contain a second heteroatom other than nitrogen; and linear or branched $C_1$-$C_6$ alkyl radicals substituted with a nitrile, ester, acyl or amide group or a group —CO—O—$R_9$—D or —CO—NH—$R_9$—D where $R_9$ is an alkylene and D is a quaternary ammonium group;
$A_1$ and $B_1$, which may be identical or different, denote polymethylene groups containing from 2 to 20 carbon atoms which may be linear or branched, saturated or unsaturated, and which may contain, linked to or intercalated in the main chain, one or more aromatic rings or one or more oxygen or sulphur atoms or sulphoxide, sulphone, disulphide, amino, alkylamino, hydroxyl, quaternary ammonium, ureido, amide or ester groups; and
$X^-$ denotes an anion derived from an inorganic or organic acid.

22. A composition according to claim 21, wherein $A_1$, $R_5$ and $R_7$ form, together with the two nitrogen atoms to which they are attached, a piperazine ring.

23. A composition according to claim 21, wherein $A_1$ denotes a linear or branched, saturated or unsaturated alkylene or hydroxyalkylene radical and $B_1$ denotes a group $(CH_2)_n$—CO—D—OC—$(CH_2)_n$—,
wherein D denotes:
a) a glycol residue of formula: —O—Z—O—, wherein Z denotes a linear or branched hydrocarbon radical or a group corresponding to one of the following formulae:

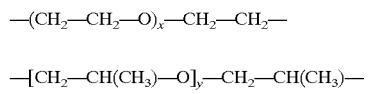

wherein x and y denote an integer from 1 to 4, representing a defined and unique degree of polymerization or any number from 1 to 4 representing an average degree of polymerization;
b) a bis-secondary diamine residue;
c) a bis-primary diamine residue of formula: —NH—Y—NH—, wherein Y denotes a linear or branched hydrocarbon radical, or alternatively the divalent radical —$CH_2$—$CH_2$—S—S—$CH_2$—CH2—; or
d) a ureylene group of formula: —NH—CO—NH—.

24. Composition according to claim 23, wherein said bis-secondary diamine residue is a piperazine derivative.

25. A composition according to claim 1, wherein said at least one non-cellulosic cationic polymer comprises quaternary polyammonium polymers consisting of units of formula (VI):

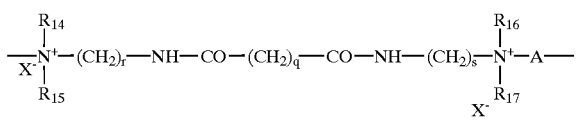

(VI)

wherein:
$R_{14}$, $R_{15}$, $R_{16}$ and $R_{17}$, which may be identical or different, denote a hydrogen atom or a methyl, ethyl, propyl, β-hydroxyethyl, β-hydroxypropyl or —$CH_2CH_2$($OCH_2CH_2$)$_p$OH radical, wherein p is equal to 0 or to an integer between 1 and 6, with the proviso that $R_{14}$, $R_{15}$, $R_{16}$ and $R_{17}$ do not simultaneously represent a hydrogen atom;
r and s, which may be identical or different, are integers between 1 and 6;
q is equal to 0 or to an integer between 1 and 34;
$X^-$ denotes an anion; and
A denotes a radical derived from a dihalide or —$CH_2$—$CH_2$—O—$CH_2$—$CH_2$—.

26. A composition according to claim 25, wherein X denotes a halide.

27. A composition according to claim 1, said at least one non-cellulosic cationic polymer comprises homopolymers or copolymers containing at least one unit chosen from:

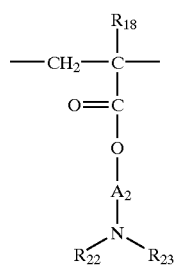 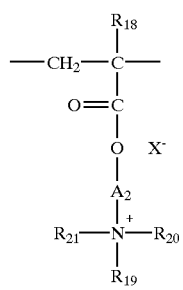

-continued

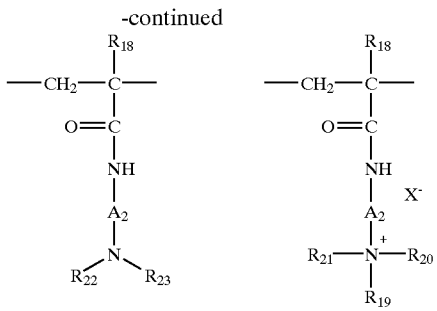

the groups $R_{18}$, which may be identical or different, denote H or $CH_3$;

the groups $A_2$, which may be identical or different, denote a linear or branched alkyl group of 1 to 6 carbon atoms or a hydroxyalkyl group of 1 to 4 carbon atoms;

the groups $R_{19}$, $R_{20}$ and $R_{21}$, which may be identical or different, denote an alkyl group of 1 to 18 carbon atoms or a benzyl radical;

the groups $R_{22}$ and $R_{23}$ denote a hydrogen atom or an alkyl group of 1 to 6 carbon atoms; and X denotes an anion.

28. A composition according to claim 27, wherein X denotes a halide.

29. A composition according to claim 1, wherein said at least one non-cellulosic cationic polymer comprises quaternary polymers of vinylpyrrolidone and of vinylimidazole.

30. A composition according to claim 1, wherein said at least one non-cellulosic cationic polymer comprises crosslinked polymers of methacryloyloxy($C_1$–$C_4$)alkyltri($C_1$–$C_4$)alkylammonium salts.

31. A composition according to claim 1, wherein said at least one non-cellulosic cationic polymer is chosen from polymers comprising polyalkyleneimines, polymers comprising vinylpyridine units, polymers comprising vinylpyridinium units, polymers comprising condensates of polyamines and of epichlorohydrin, polymers comprising quaternary polyureylenes, and polymers comprising chitin derivatives.

32. A composition according to claim 31, wherein said polyalkyleneimines are chosen from polyethyleneimines.

33. A composition according to claim 1, wherein said at least one non-cellulosic cationic polymer comprises dimethyldiallylammonium chloride homopolymers or copolymers of dimethyldiallylammonium chloride and of acrylamide.

34. A composition according to claim 1, wherein said at least one non-cellulosic cationic polymer comprises polymers consisting of repeating units corresponding to the formula (V):

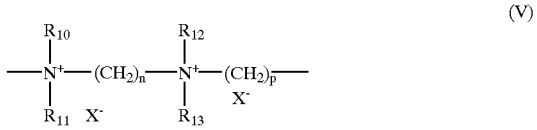

wherein $R_{10}$, $R_{11}$, $R_{12}$ and $R_{13}$, which may be identical or different, denote an alkyl or hydroxyalkyl radical containing from 1 to 4 carbon atoms approximately; n and p are integers ranging from approximately 2 to 20 and $X^-$ is an anion derived from an inorganic or organic acid.

35. A composition according to claim 1, wherein said at least one anionic surfactant is present in a concentration ranging from 1 and 30% by weight, relative to the total weight of the composition.

36. A composition according to claim 1, wherein said at least one anionic surfactant is present in a concentration ranging from 3 and 15% by weight, relative to the total weight of the composition.

37. A composition according to claim 1, wherein said at least one non-cellulosic cationic polymer is present in a concentration ranging from 0.001% and 10% by weight relative to the total weight of the composition.

38. A composition according to claim 1, wherein said at least one non-cellulosic cationic polymer is present in a concentration ranging from 0.005% and 5% by weight relative to the total weight of the composition.

39. A composition according to claim 1, wherein said at least one non-cellulosic cationic polymer is present in a concentration ranging from 0.01% and 3% by weight relative to the total weight of the composition.

40. A composition according to claim 1, further comprising at least one additional surfactant chosen from an anionic surfactant, a cationic surfactant, a nonionic surfactant, and an amphoteric surfactant.

41. A composition according to claim 40, wherein said at least one additional surfactant is present in a concentration ranging from 0.5% and 40% by weight, relative to the total weight of the composition.

42. A composition according to claim 40, wherein said at least one additional surfactant is present in a concentration ranging from 5% and 20% by weight, relative to the total weight of the composition.

43. A composition according to claim 1, further comprising at least one additive chosen from thickeners, fragrances, nacres, preserving agents, sunscreens, anionic polymers, nonionic polymers, amphoteric polymers, cationic polymers with a charge density of less than 2 meq/g, proteins, protein hydrolysates, ceramides, pseudoceramides, a fatty acid containing linear or branched $C_{16}$–$C_{40}$ chains, hydroxy acids, vitamins, panthenol, silicones, plant oils, mineral oils, synthetic oils and antidandruff agents.

44. A composition according to claim 43, wherein said fatty acid containing linear or branched $C_{16}$–$C_{40}$ chains is 18-methyleicosanoic acid.

45. A composition according to claim 1, wherein said composition is in a cosmetically acceptable aqueous medium.

46. A composition according to claim 1, wherein said composition is in the form of a shampoo, a composition for washing the skin, a rinse-out or leave-in conditioner, permanent-waving the hair, a composition for straightening the hair, a composition for dyeing the hair, or a composition for bleaching the hair.

47. A composition according to claim 1, wherein said composition is in the form of a rinse-out composition to be applied before or after dyeing, bleaching, permanent-waving or straightening the hair, or between the two steps of a permanent-waving or hair-straightening operation.

48. A process for washing keratin substances comprising applying to said keratin substances a cosmetic composition comprising at least one non-cellulosic cationic polymer with a cationic charge density of greater than or equal to 2 meq/g, and at least one anionic surfactant chosen from 2-hydroxyalkyl ether carboxylic acid and salts thereof, and rinsing said washed keratin substances.

49. A process according to claim 48, wherein said keratin substances are hair.

50. A process for the treatment of keratinous substances comprising applying to said keratin substances a cosmetic composition comprising at least one non-cellulosic cationic polymer with a cationic charge density of greater than or equal to 2 meq/g, and at least one anionic surfactant chosen from 2-hydroxyalkyl ether carboxylic acid and salts thereof.

51. A process according to claim 50, wherein said keratin substances are hair.

52. A process according to claim 50, further comprising rinsing said treated keratin substances.

* * * * *

UNITED STATES PATENT AND TRADEMARK OFFICE
CERTIFICATE OF CORRECTION

PATENT NO. : 6,511,669 B1  Page 1 of 1
DATED : January 28, 2003
INVENTOR(S) : Nathalie Garnier et al.

It is certified that error appears in the above-identified patent and that said Letters Patent is hereby corrected as shown below:

Column 13,
Line 57, "according claim" should read -- according to claim --.

Column 14,
Line 15, "bis-haloacyidiamine" should read -- bis-haloacyldiamine --.

Column 17,
Line 13, before "the groups", insert -- wherein: --.
Lines 44-45, "dimethyidiallylammonium" should read -- dimethyldiallylammonium --.

Column 18,
Line 46, "fafty" should read -- fatty --.

Signed and Sealed this

Eighth Day of April, 2003

JAMES E. ROGAN
*Director of the United States Patent and Trademark Office*